United States Patent
Adler et al.

(10) Patent No.: US 8,967,186 B2
(45) Date of Patent: Mar. 3, 2015

(54) FLUID SPILL CONTAINMENT, LOCATION, AND REAL TIME NOTIFICATION DEVICE AND SYSTEM

(71) Applicants: Jeffrey Scott Adler, Beaconsfield (CA); Harold Russell Baird, Marietta, GA (US)

(72) Inventors: Jeffrey Scott Adler, Beaconsfield (CA); Harold Russell Baird, Marietta, GA (US)

( * ) Notice: Subject to any disclaimer, the term of this patent is extended or adjusted under 35 U.S.C. 154(b) by 193 days.

(21) Appl. No.: 13/694,752

(22) Filed: Jan. 2, 2013

(65) Prior Publication Data

US 2014/0182706 A1 Jul. 3, 2014

Related U.S. Application Data

(60) Provisional application No. 61/743,848, filed on Sep. 13, 2012.

(51) Int. Cl.

| | |
|---|---|
| *F16L 55/07* | (2006.01) |
| *F16L 7/02* | (2006.01) |
| *F16L 9/18* | (2006.01) |
| *G01N 3/00* | (2006.01) |
| *E21B 49/00* | (2006.01) |
| *G01F 1/00* | (2006.01) |
| *G01M 3/28* | (2006.01) |

(52) U.S. Cl.
CPC ... *F16L 7/02* (2013.01); *F16L 9/18* (2013.01); *G01N 3/00* (2013.01); *E21B 49/00* (2013.01); *G01F 1/00* (2013.01); *G01M 3/283* (2013.01)
USPC ...................... 137/312; 251/129.04; 340/605

(58) Field of Classification Search
USPC ........ 137/312, 15.11; 251/129.04; 73/40.5 R; 141/86; 340/605
See application file for complete search history.

(56) References Cited

U.S. PATENT DOCUMENTS

| | | | |
|---|---|---|---|
| 4,786,088 A | 11/1988 | Zui | |
| 6,575,206 B2* | 6/2003 | Struthers et al. | 137/312 |
| 7,500,489 B2* | 3/2009 | Folkers | 137/312 |
| 7,527,065 B2* | 5/2009 | Ingram | 137/312 |
| 7,583,198 B2* | 9/2009 | Kates | 137/312 |
| 8,130,107 B2* | 3/2012 | Meyer | 137/312 |
| 8,291,928 B2* | 10/2012 | Reid et al. | 137/68.14 |
| 8,786,451 B2* | 7/2014 | Lee | 137/312 |
| 2003/0160447 A1 | 8/2003 | Stark et al. | |

FOREIGN PATENT DOCUMENTS

CN 101555991 A 10/2009

* cited by examiner

*Primary Examiner* — Kevin Lee

(57) ABSTRACT

Described herein is an autonomous fluid spill containment device for a pipeline having a carrier conduit for transporting a fluid and a containment conduit located around the carrier conduit to define an interstitial space for receiving fluid spilled from the carrier conduit. The device comprises a spilled fluid barrier for stopping spilled fluid flow. The fluid barrier is located in the interstitial space and extending between the carrier conduit and the containment conduit. A spilled fluid sensor is located in the interstitial space to detect spilled fluid flowing in the containment conduit. A network monitor that interfaces for communicating with an operator's data collection, analysis and reporting systems. A sensor network is connected to the fluid sensor for communicating spilled fluid sensor and location data from the sensor to the network monitor so as to alert the operator to the location of the spilled fluid in real time.

50 Claims, 12 Drawing Sheets

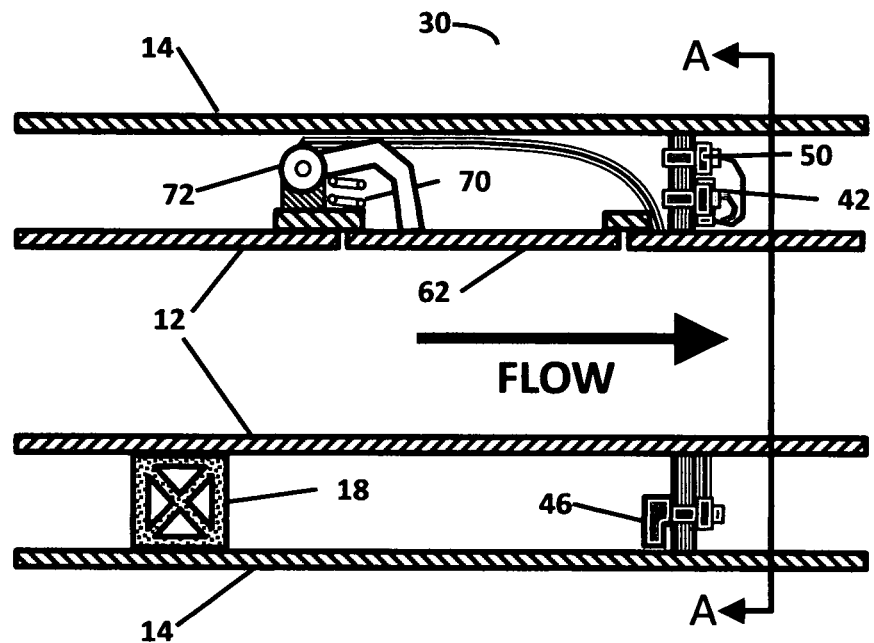
Figure 5
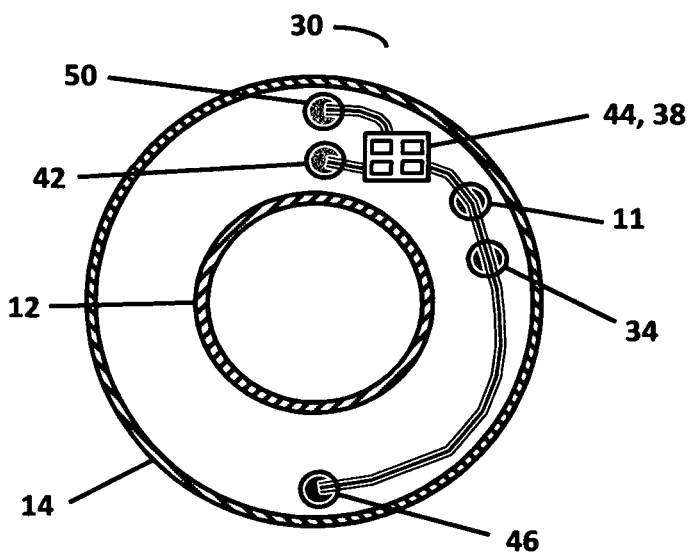
Figure 5A Section A-A

FLUID SPILL CONTAINMENT, LOCATION, AND REAL TIME NOTIFICATION DEVICE AND SYSTEM

CROSS REFERENCE TO RELATED APPLICATIONS

Applicants hereby claim priority from U.S. patent application Ser. No. 61/743,848, filed Sep. 13, 2012, the entire contents of which is hereby incorporated by reference.

TECHNICAL FIELD

The present relates to fluid transportation using pipelines, and more particularly to a fluid spill containment, accurate location, and real time notification device and system for use with pipelines.

BACKGROUND

Pipeline transportation of energy sources has never been so important to the energy infrastructure and consumption of developing nations. Our economies and base of manufacturing rely heavily on the safe and timely provision of energy that may be transported through pipelines in different forms. This quest for energy sources has made the necessity of pipelines an inherent component in our society as a result of their ability to economically transport large volumes of liquids and gases. From crude oil to liquid natural gas, to tar sand oil: the reliable delivery of these valuable commodities for processing or immediate use has never been so important to powering our homes, businesses, towns, cities and nations. The transportation of energy sources often occurs over vast distances through rough terrain, difficult environments, important agricultural lands, valuable ecosystems, extreme weather, hydrologically sensitive areas, and potentially unstable regions.

However, an inherent problem with energy source pipelines is the catastrophic impact a spill or leak can have on our environments, ecosystems, humans and wildlife. The risk to valuable water reserves including but not limited to: the wetlands, streams, rivers, and aquifers which in some circumstances is the main source of natural clean drinking water for large segments of population bases is immeasurable. Further, as a result of the range of damage that may be caused due to the potentially toxic transported materials, the damage can persist for years.

In 2007, there were 161,000 miles of onshore pipeline transporting hazardous materials (chiefly petroleum products) in the US. From 2007 to 2011, significant spillage incidents averaged 117 per year, and released an average of 80,000 barrels of hazardous product per year into the environment for a total spillage of approximately 400,000 barrels. Other countries and nations throughout the world have experienced similar spill occurrences per mile of pipeline. There is now a great need for a pipeline system that will not only reduce the severity and occurrences of such releases, but concurrently and autonomously actively monitors a pipeline to enable the owner/operator to be able to know in real time precisely where and when there is a concern, exactly what the issue is at any specific location throughout the entire pipeline, and the appropriate response needed to affect said concern. What is needed is an effective containment, autonomous, self monitoring, and active notification system.

Safe pipelines are the key to moving forward in our energy dependant world. The majority of existing petrochemical pipelines in use are fabricated as single wall pipes, may be buried or above ground, and may have an insulating jacket. Whilst a single wall pipe has lower construction and repair costs than a double walled type, single wall pipe failures can release transported toxic materials to the surroundings with devastating results. Significant releases can occur before detection, resulting in catastrophic damage to the environment, humans and wildlife, as well as loss of goodwill, costly clean up operations and litigation against the pipeline owner/operator.

A number of pipeline leak detection systems have been designed to address the aforesaid problems, some of which are described below:

U.S. Pat. No. 6,032,699 by Graeber et al uses a dual wall system with a pressurized gas or liquid in the containment pipe. Leaks are detected by pressure sensors at sealed pipe segments, and a local audio or visual alarm is set. The design intent is for gas station fuel distribution. This design is not suitable for long pipelines due to the limited type of sensors and inability to communicate over long distances.

U.S. Pat. No. 5,433,191 by McAtamney uses a dual wall system zoned off by annular rings and detects the presence of liquids, including hydrocarbons using capacitive sensors. Each sensor is connected to a common panel for local audio and visual alarm indications. The design intent is for a storage tank next to an industrial plant. This design is not suitable for long pipelines due to the limited type of sensors and inability to communicate over long distances.

U.S. Pat. No. 6,970,808 by Abhulimen et al uses general pipeline parameters such as flow and pressure at monitoring stations along the line as inputs to central analysis and simulation algorithms to deduce when a spill has occurred. Since direct measurement at a spill location is not used, the method is subject to false alarms such as an operator changing a valve position, and has insufficient accuracy to detect small but significant leaks. Also, the method has no provision for spill containment.

U.S. Pat. No. 7,500,489 by Folkers uses a dual wall pipeline with brine in the container pipe at a higher pressure than the carrier pipe. The brine chambers are connected via tubes to a gas-brine reservoir, and leaks are detected by a float in the reservoir. To minimize brine requirements, the interstitial space is small, but this makes the example subject to false alarms from carrier pipe expansion and contraction due to carrier transported gas or liquid pressure or temperature changes. The use of brine also restricts use to non-corrosive carrier pipe materials such as fiberglass. Using a non-corrosive liquid such as glycol risks releasing toxic material to the environment. The small interstitial space also offers little protection for the carrier pipe from excavation equipment accidental damage.

U.S. Pat. No. 7,441,441 by Omer uses a dual wall pipeline with hydraulic fluid in the container pipe at a higher pressure than the carrier pipe. A break in the carrier pipe causes a hydraulic fluid pressure drop which is sensed. The pipeline is segmented by valve stations which close off the pipeline flow when the pressure drop is sensed. This method cannot distinguish between carrier pipe and container pipe leaks, and has a great potential for leaking hydraulic fluid into the environment. The system has no provision for reporting a leak, and it's isolation capability is limited to the distance between valve stations.

U.S. Pat. No. 6,489,894 by Berg uses a vacuum between the inner and outer pipes and a vacuum switch manifolded among more than one container section to determine when a leak has occurred. The patent refers to previous art which did not use a manifold, and therefore were more costly. The design intent, despite the title, is for use in storage tanks, not long pipelines. Scaling Berg's approach (or any of his referenced art approaches) to typical pipelines is cumbersome at best, and Berg's approach provides poor leak isolation information.

U.S. Pat. No. 6,123,110 by Smith et al provides a method for rehabilitating a single wall pipe into a double wall pipe by inserting a new smaller diameter pipe with stud spacers inside the existing pipe. The spacers provide for installing a leak detection system, examples of which are referred to but not well described. A manhole adapter is described. Smith's approach disadvantageously uses an old pipe for containment which is likely to fail when pressurized by a leak from the new inner pipe, and it makes no claims for leak isolation and reporting capability.

US Patent 2005/0212285 by Haun describes a method for reducing stresses in joints between the inner and outer pipe, and makes no claims for leak detection, isolation and reporting.

U.S. Pat. No. 3,943,965 by Matelena is a triple wall pipe which passes a glycol coolant between the outer and middle pipe to prevent hot oil or petroleum gas from melting the surrounding permafrost. The space between the middle pipe and carrier pipe is a vacuum insulator. Hydrometer and pressure sensors in the vacuum detect leaks from the coolant and carrier pipes. A photoelectric sensor detects changes in the glycol coolant transparency as an additional leak detection method. An oil/glycol separator and pump return leaked oil back into the carrier pipe. Matelena's approach is cumbersome to implement due to the triple wall construction, the large volumes of glycol needed, and the leak prone plumbing needed to cool and distribute the glycol. There is no method defined for preventing the glycol from leaking into the permafrost. The oil/glycol separator is unlikely to be able to accommodate large flow rate oil leaks. And there is no method defined for collecting and reporting sensor data.

Thus, there is a need for an improved pipeline which addresses the above-noted problems.

BRIEF SUMMARY

We have designed a fluid spill containment device and system for pipelines carrying energy sources which significantly reduces the probability and magnitude of pipeline releases as a result of its complete integrity and safety management program through containment in a dual wall pipe, instrumentation to sense a release and its accurate location, as well as a real time reporting network to trigger specific repair responses. Whilst the device and system may be more expensive to put in place than a single wall pipeline, its superior autonomous self monitoring/detection, containment and reporting system significantly cuts down on valuable product loss and spill damage to the environment and associated costs, reduces lifetime maintenance costs, facilitates construction approval, and improves goodwill in the community. Advantageously, the device and system is retrofittable into conventional pipe designs presently used in the pipeline industry whereby adaptations are made to these pipes to enable them to serve as the main carrier pipe for the energy source transported.

Accordingly, in one aspect there is provided an autonomous fluid spill containment device for a pipeline having a carrier conduit for transporting a fluid and a containment conduit located around the carrier conduit to define an interstitial space for receiving fluid spilled from the carrier conduit, the device comprising:

a spilled fluid barrier for stopping spilled fluid flow, the fluid barrier being located in the interstitial space and extending between the carrier conduit and the containment conduit;

a spilled fluid sensor located in the interstitial space to detect spilled fluid flowing in the containment conduit;

a network monitor that interfaces for communicating with an operator's data collection, analysis and reporting systems; and a sensor network connected to the fluid sensor for communicating spilled fluid sensor and location data from the sensor to the network monitor so as to alert the operator to the location of the spilled fluid in real time.

In one example, the spilled fluid sensor is located at a lower portion of the containment conduit.

In one example, the spilled fluid sensor is mounted on the spilled fluid barrier.

In one example, the spilled fluid sensor is mounted in a sensor station.

In one example, a sensor station is mounted exterior of the containment pipe, the sensor station being in communication with the spilled fluid sensor. The sensor station includes:
a) a housing;
b) a purge member located in the housing and in fluid communication with the interstitial space and a spilled fluid sensor; and
c) a sensor station network including a controller located in the housing, the controller being in communication with a purge member pressure sensor, a local status indicator for further facilitating accurate location of a spill/seepage, and the spilled fluid sensor.

In one example, the sensor station further includes a plurality of sensors interconnecting with the controller and the sensor network. The sensors include a pressure sensor, a temperature sensor, a fluid sensor, a position sensor, and a hydrocarbon sensor whereby one or more may be implemented and activatable.

In one example, the sensor station further includes a network power and data bus interconnected to the sensors.

In one example, the sensor station further includes a repeater.

In one example, the network monitor is interconnected with the sensor station network and includes a network modem, a network interface and a display/control.

In one example, the network monitor is in communication with an operator land network. The operator land network is in communication with an auto emergency shutdown.

In one example, the network monitor is in communication with an operator analysis and response center, or like facility.

In one example, the device may include a spill return door assembly located upstream from the spilled fluid barrier. The spill return door assembly, when implemented, includes a spill return door resiliently connected to the carrier conduit and is urged against an interior portion of the carrier conduit adjacent a spill opening. The spill door assembly includes a mounting column and a door spring connected to the spill return door.

In one example, the door spring is located in the housing exterior of the containment conduit.

In another example, the door spring is located in the containment conduit.

In one example, the spill door assembly includes a spill door position sensor.

In one example, a sensor station is mounted interior of the containment pipe, the sensor station being in communication with the spilled fluid sensor. The sensor station includes a sensor station network having a plurality of sensors interconnecting with the controller and the sensor network. The sensors include a pressure sensor, a temperature sensor, a fluid sensor, a position sensor, and a hydrocarbon sensor wherein one or more of the sensors may be implemented and activatable.

In one example, the sensor station further includes a network power and data bus interconnected to the sensors and in communication with an external sensor station providing autonomous or alternate power.

In one example, the sensor station further includes a repeater.

In one example, the network monitor is interconnected with the sensor station network and includes a network modem, a network interface and a display/control.

In one example, the network monitor is in communication with an operator land network.

In one example, the operator land network is in communication with an auto emergency shutdown.

In one example, the network monitor is in communication with an operator analysis and response center, or like facility.

In one example, the device may include a spill return door assembly located upstream from the spilled fluid barrier.

In one example, the spill return door assembly includes a spill return door assembly, when implemented, is resiliently connected to the carrier conduit and is urged against an interior portion of the carrier conduit adjacent a spill opening. The spill door assembly includes a mounting column and a door spring connected to the spill return door. The spill door assembly includes a spill door position sensor.

In one example, the device is for a pipeline that is located above ground, water or ice.

In one example, the device is for a pipeline that is located below ground or ice.

In one example, the device is for a pipeline that is located underwater.

In one example, the fluid includes gas, chemicals such as synthetic, organic, inorganic; and natural fluids including food liquids; liquefied natural gas, liquefied gas including propane and butane; crude oil, water, petroleum, light oil, or tar sands oil.

According to another aspect, there is provided an autonomous sensor and reporting network for monitoring pipeline spillage, the network comprising:
  a) an autonomous fluid spill containment device, as described above; and
  b) a network interface in communication with the device, the network interface being configured to transmit sensor and location data from the device to an analysis and response center, the center being located to receive data over a wired or wireless network from the device such that real time data received at the center indicative of a fluid spill triggers a response at the center.

In one example, a satellite network is in communication with the device to relay data from the device to the center.

In one example, a wireless land network is in communication with the device to relay data from the device to the center.

In one example, a wired land network is in communication with the device to relay data from the device to the center.

According to another aspect, there is provided an autonomous sensor and reporting system for monitoring pipeline spillage, the system comprising:
  a) an autonomous fluid spill containment device having a carrier conduit for transporting a fluid and a containment conduit located around the carrier conduit to define an interstitial space for receiving fluid spilled from the carrier conduit, the device having a spilled fluid barrier for stopping spilled fluid flow, the fluid barrier being located in the interstitial space and extending between the carrier conduit and the containment conduit; a spilled fluid sensor located in the interstitial space to detect spilled fluid flowing in the containment conduit; a network monitor that interfaces for communicating with an operator's data collection, analysis and reporting systems; and a sensor network connected to the fluid sensor for communicating spilled fluid sensor and location data from the sensor to the network monitor so as to alert the operator to the location of the spilled fluid in real time;
  b) an active network interface in communication with the device, the network interface being configured to transmit sensor and location data from the device to an analysis and response center, the center being located to receive data over the operator's selection of wired and wireless networks from the device such that real time data received at the center indicative of a fluid spill triggers a response at the center; and
  c) a real time self-monitoring and reporting system that determines sensor station health status, sensor data and network status in real time.

In one example, the wireless network is a satellite network in communication with the device to relay data from the device to the center.

In one example, a wireless land network is in communication with the device to relay data from the device to the center.

In another example, a wired land network is in communication with the device to relay data from the device to the center.

In another example, a dual wall pipe with an outer casement spilled fluid barrier is utilized.

In one example, the sensor stations include a plurality of sensors that may be implemented and activatable including: pressure, temperature, fluid, position, and hydrocarbon.

In one example, the system may implement a power supply that is a conventional energy supply or a solar panel, battery and charger.

In one example, the system may include a spill door to facilitate transporting material from the outer containment conduit into the carrier conduit.

In one example, the local status indicator is a Light Emitting Diode (LED).

BRIEF DESCRIPTION OF THE DRAWINGS

In order that the discovery may be readily understood, embodiments are illustrated by way of example in the accompanying drawings.

FIG. 5 is a longitudinal cross sectional view of a pipeline section showing an internal sensor station;

FIG. 5A is cross sectional view taken along lines 5A-5A' of FIG. 5;

DETAILED DESCRIPTION

As used herein, the term "fluid" is intended to mean gas, natural gas; liquid, including chemicals, such as for example, synthetic, organic and inorganic including natural food liquids, crude oil, petroleum, tar sand oil, and water, liquefied gas, such as propane, butane, liquefied natural gas, and the like.

Figure 1:
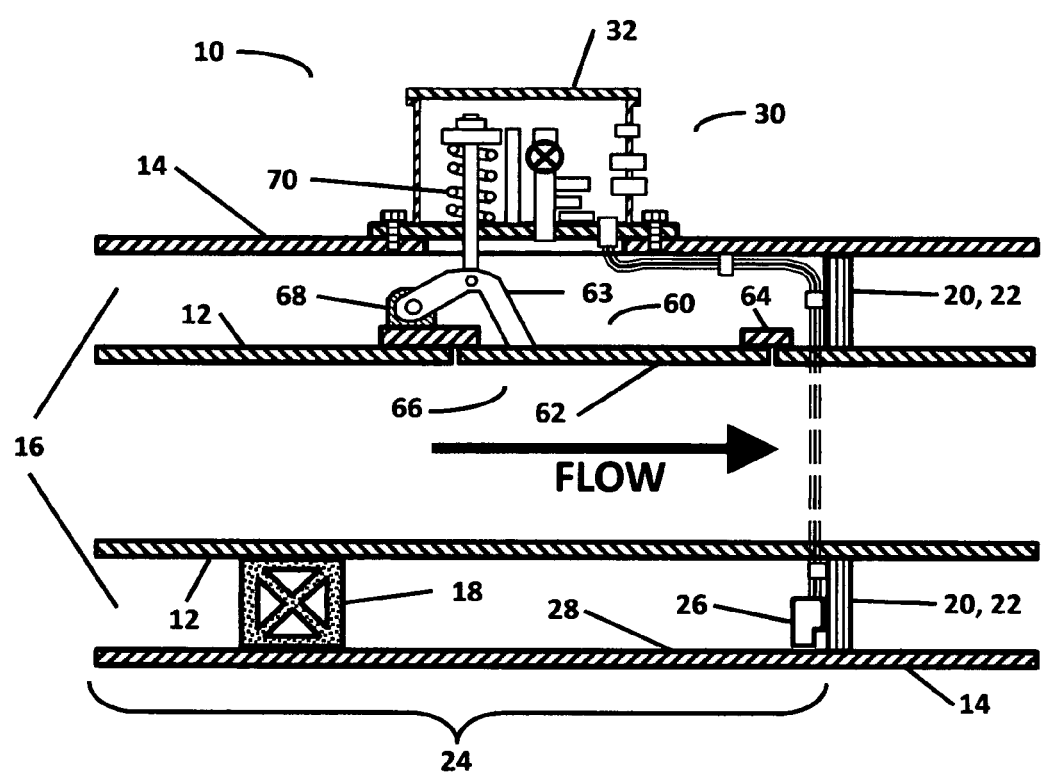
FIG. 1 is a longitudinal cross sectional view of a pipeline section showing a spill containment device and external sensor station in a no spill configuration.
Figure 2:
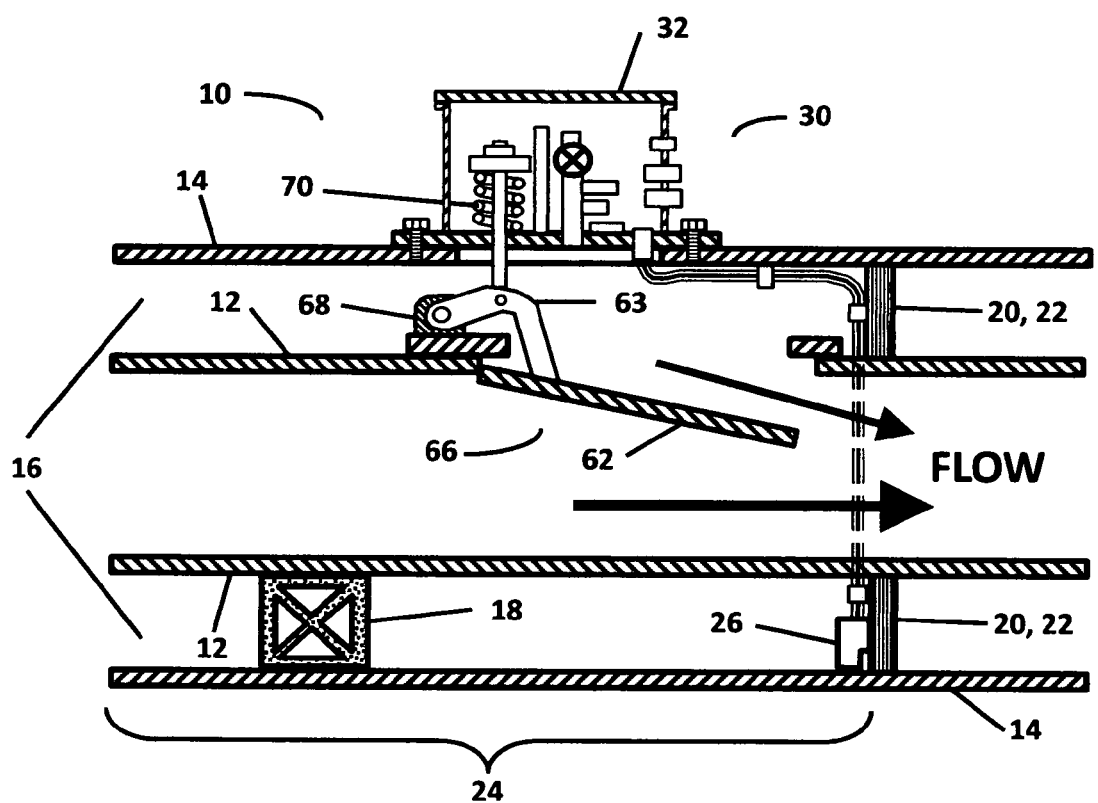
FIG. 2 is a longitudinal cross sectional view of the pipeline section showing the spill containment device and external sensor station in a spill configuration.

Referring to FIGS. 1 and 2, there is illustrated generally at 10 a fluid spill containment device. Broadly speaking, the device 10 comprises a double wall pipeline which includes an inner carrier conduit (pipe) 12 and an outer containment conduit (pipe) 14 which encases the carrier pipe 12, and which defines an interstitial space 16 around the carrier pipe 12. The carrier pipe 12 carries the fluid therealong. The interstitial space 16 receives fluid that spills from the carrier pipe 12 in the event that the carrier pipe 12 breaks or is structurally compromised. A plurality of spacers 18 are disposed substantially along the entire length of the pipeline and maintain separation between pipes 12, 14. A spilled fluid barrier 20 is located between the carrier pipe 12 and the containment pipe 14 and stops flow of fluid that spills into the interstitial space 16 from further flow downstream. The spilled fluid barrier 20 is an annular bulkhead 22 that is welded to the carrier pipe 12 and sealed to the containment pipe 14 to define separate release containment sections 24 along the pipeline. A spilled fluid sensor 26 is located in the interstitial space 16 to detect spilled fluid flowing in the containment pipe 14. Typically, the spilled fluid sensor 26 is located at a lower portion 28 of the containment pipe 14. In the example shown, the spilled fluid sensor 26 is mounted on the spilled fluid barrier 20.

Figure 10:
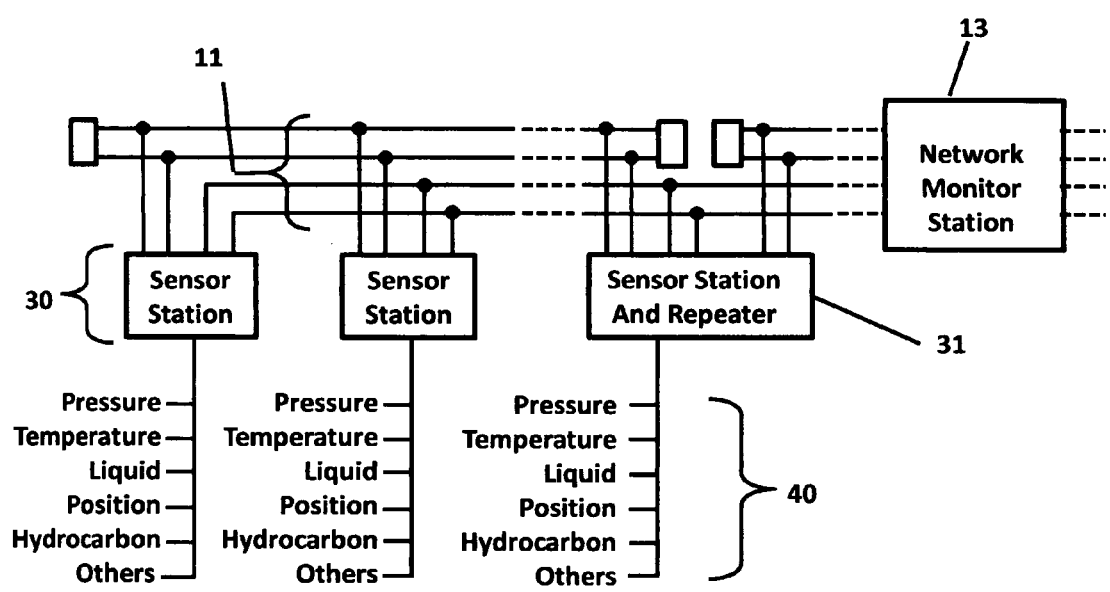
FIG. 10 is a diagram of a sensor station network.

Referring now to FIG. 10, a sensor network 11 is connected to the sensors 40 for communicating spilled fluid data from the sensors 40 to a network monitor 13 so as to alert an operator to the location of the spilled fluid in real time.

Referring again to FIGS. 1 and 2, and now 8, a sensor station 30 is mounted on the exterior of the containment pipe 14. The sensor station 30 is in communication with the spilled fluid sensor 26. The sensor station 30 includes a housing 32 and a sensor station network 34. The sensor station network 34 includes a purge member 36 located in the housing 32 and in fluid communication with the interstitial space 16. A temperature sensor 44 and sensor station controller 38 are located in the housing 32 and is connected to the purge member pressure sensor 36 and the spilled fluid sensor 26. In the example shown in FIG. 8, the sensor station 30 includes a plurality of sensors 40 interconnecting with the controller 38 and the sensor network 11. The sensors 40 include a pressure sensor 42, a temperature sensor 44, a fluid sensor 46, a position sensor 48, and a hydrocarbon sensor 50, one or more of which can be implemented and activated. A penetration connector 52 is connected to the controller 38 and disposed in the containment pipe 14 and connected to the sensor 26 via wires 54. A network power and data bus 56 interconnects the sensor stations.

Referring now to FIGS. 1 and 2, a spill return door assembly 60 is located upstream from the spilled fluid barrier 20. The spill return door assembly 60 includes a spill return door 62 resiliently connected to the carrier pipe 12 and is urged against an interior portion 64 of the carrier pipe 12 adjacent a spill opening 66. The spill door assembly 60 includes a mounting column 68 and a door spring 70 connected to the spill return door 62. In the example illustrated in FIGS. 1 and 2, the door spring 70 is located in the housing 32 that is located on the exterior of the containment pipe 14. The spill return door 62 is hingeably connected to a pivoting arm 63 at the upstream end and connected to the door spring 70 external to the containment pipe. The spill door 62 is contoured to the carrier pipe 12 shape to limit obstruction to normal material flow and the passage of devices such as pigs. The spill door 62 is sealed (urged) against a restraint flange to prevent material flow from the carrier to the containment pipe. The sensor 26 is located at the containment pipe bottom interior and has a cable connection to the sensor station. In the event of an upstream material release from the carrier pipe, the fluid will flow into the containment pipe 14, then back into the carrier pipe 12 through the spill door 62, and be detected by the liquid and sensor station sensors.

Figure 3:
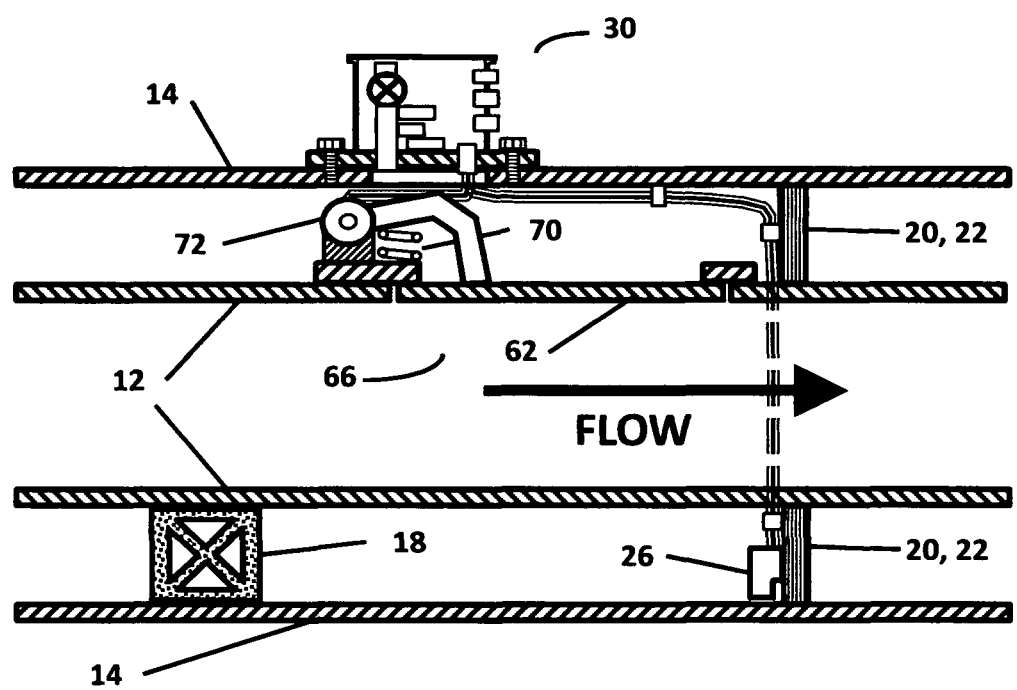
FIG. 3 is a longitudinal cross sectional view of a pipeline section showing the spill containment device and an internal spring door in a no spill configuration.
Figure 4:
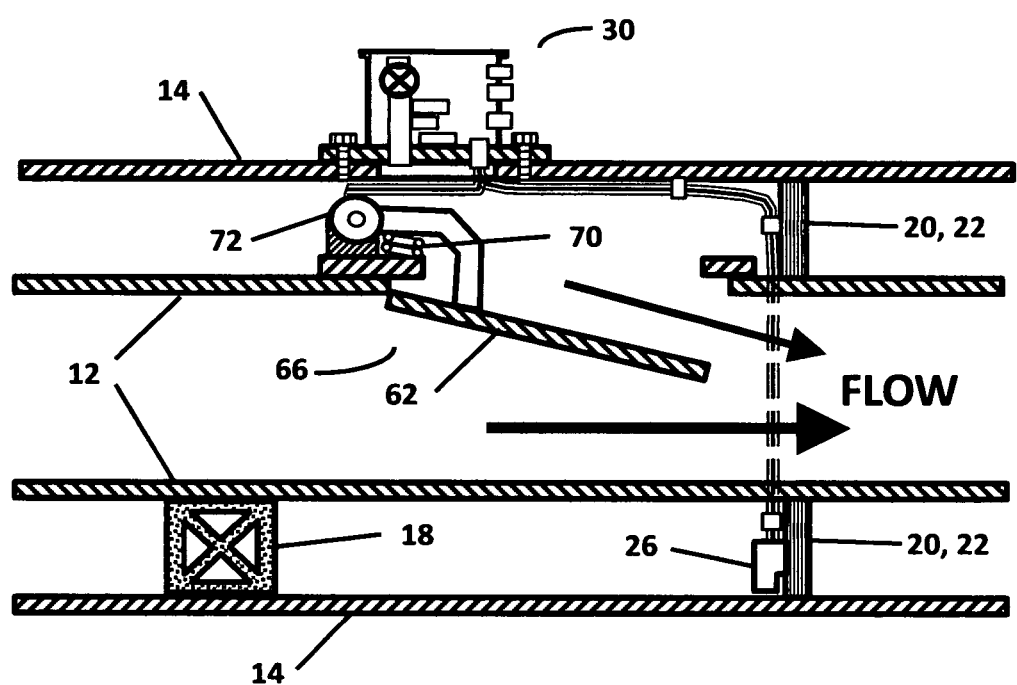
FIG. 4 is a longitudinal cross sectional view of a pipeline section showing the spill containment device and the internal spring door in a spill configuration.

Referring now to FIGS. 3 and 4, the sensor station 30 is mounted exterior of the containment pipe 14 and is in communication with the spilled fluid sensor(s). The door spring 70 is located within the containment pipe 14 to eliminate one penetration into the sensor station 30, and provide for a smaller sensor station 30. A rotary sensor (a door position sensor) 72 located on the door hinge provides a door position signal to the sensor station 30.

Referring to FIGS. 5 and 5A, an alternate internal sensor station embodiment is illustrated suitable for use underwater (submersible pipeline) or located under a non-removable overburden such as a roadway, railroad or airport. This embodiment uses the door spring 70 and the sensor station 30 within the containment pipe 14. The sensor station 30 is mounted on the annular bulkhead along with all sensors except the door position sensor. The door position sensor 72 communicates with the sensor station controller 38 using door sensor connector 34. The network power and data bus 11 runs inside the containment pipe, passing through connectors on the annular bulkheads, and exits the containment pipe 14 at a network monitor station.

Figure 6:
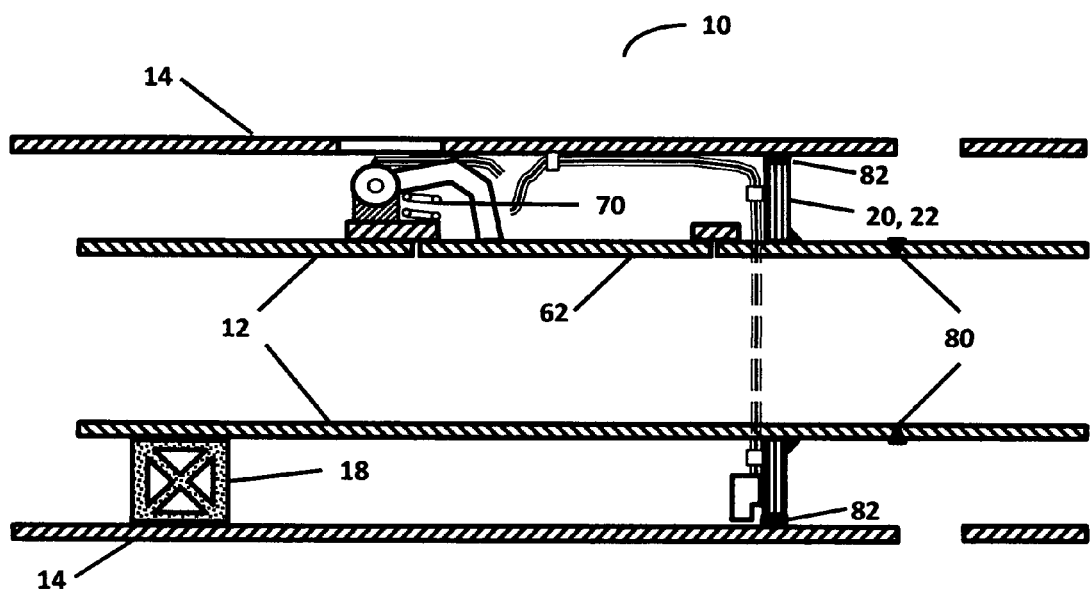
FIG. 6 is a longitudinal cross sectional view of a pipeline section showing a carrier pipe weld.
Figure 7:
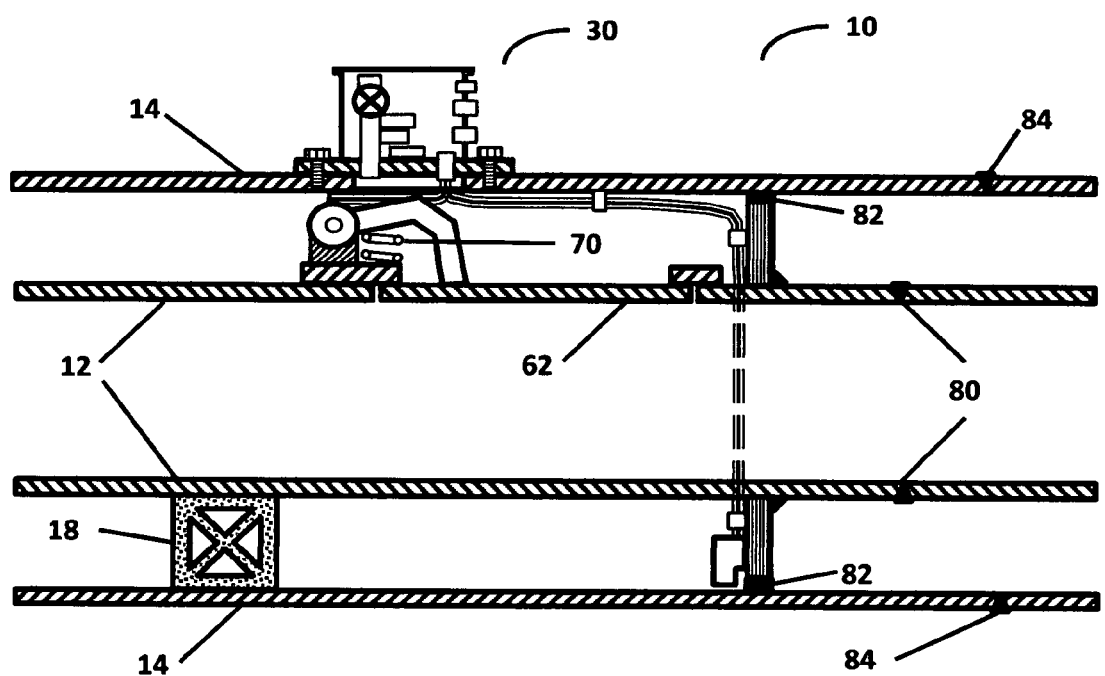
FIG. 7 is a longitudinal cross sectional view of a pipeline section showing a containment pipe weld.

Referring to FIGS. 6 and 7, field assembly of the device 10 is illustrated. The internal door spring 70 and external sensor station 30 are illustrated by way of example. One skilled in the art will recognize that a similar assembly can be used for the external door spring and internal sensor station example. The device 10 is assembled by first sliding the containment pipe 14 rearwardly, leaving a gap to allow the adjoining carrier pipes 12 to be welded together at 80. The internal sensor station connections are then made. The containment pipe 14 is then slid forward into position and the adjoining containment pipes 14 welded together at 84. The annular ring seal 82 allows the containment pipe 14 to be slid without compromising the separation of containment sections. The external sensor station 30 and related sensor network segment can then be installed at this time or later.

Still referring to FIGS. 6 and 7, the device 10 is easily assembled to join a conventional single wall pipe. This may be done in circumstances where the operator of the pipeline needs the device 10 to join up with a previously existing line that is now traversing or in order to traverse some ecologically sensitive areas. The carrier pipe 12 size should be the same as the single wall pipe. The carrier pipe 12 is welded to the single wall pipe, and an annular transition cap is welded at the containment pipe 14 end to insure sanctity of the containment pipe 14 and complete airtight enclosure.

Figure 8:
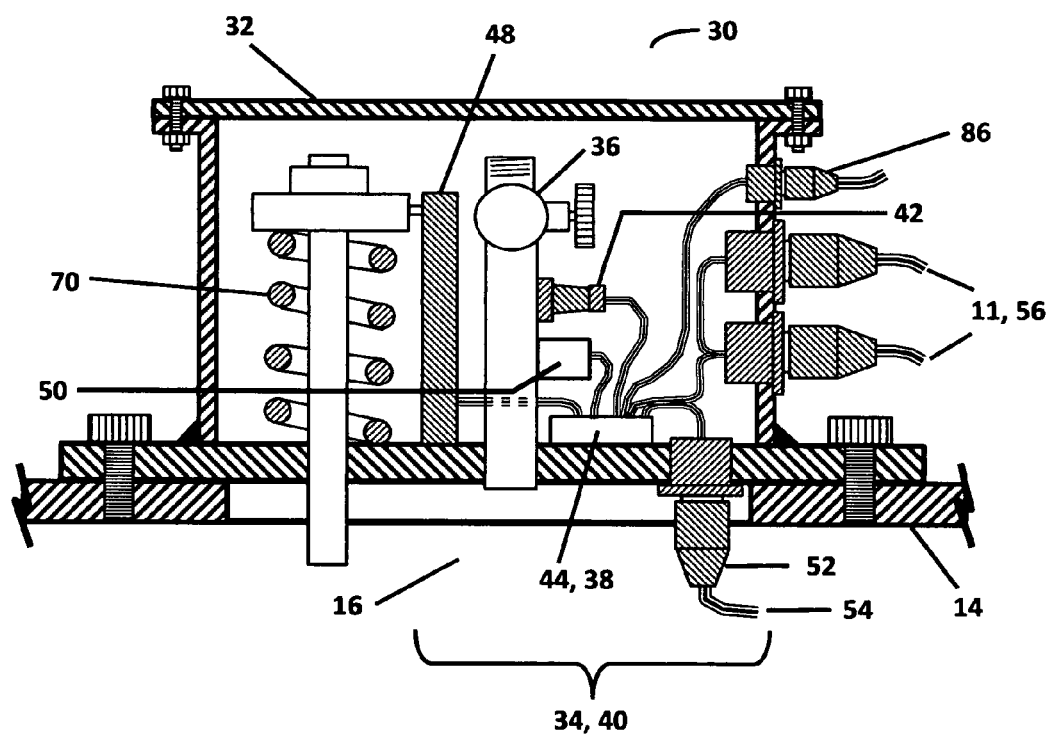
FIG. 8 is a cross sectional detailed view of an external spring sensor station.
Figure 9:
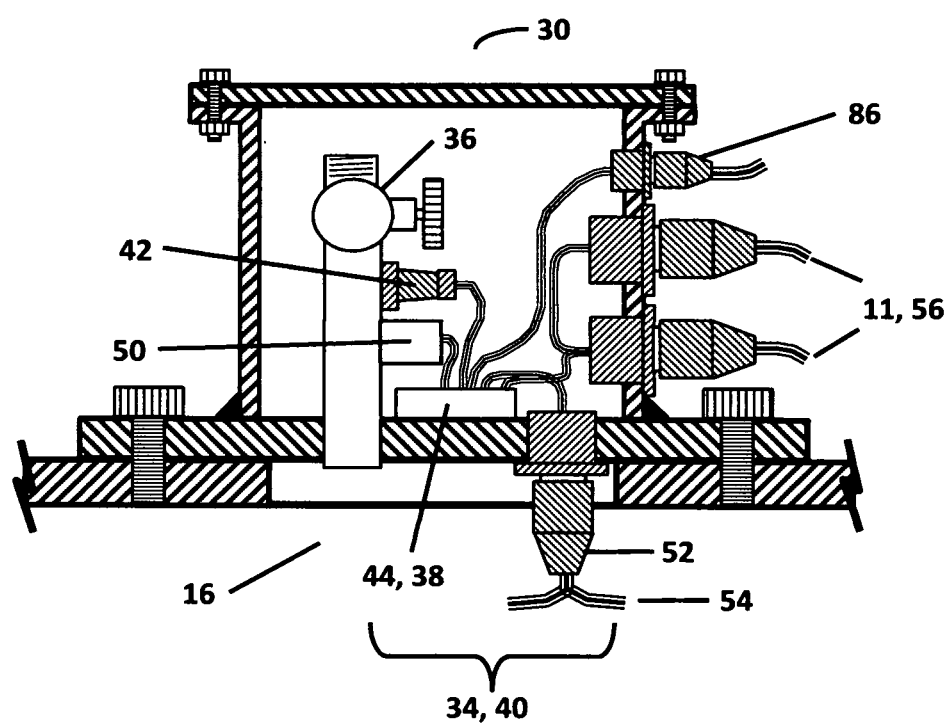
FIG. 9 is a cross sectional detailed view of an internal spring sensor station.

Referring now to FIGS. 3, 8 and 9, the sensor station for the external door spring includes a door position sensor 48 in communication with the sensor station controller 38. In FIG. 9, the internal door position sensor 72 wires are included with the liquid sensor 26 wires 54 in the penetration connector 52. A purge member 36 allows the evacuation of moisture from the containment pipe for corrosion control, and pressurizing the containment pipe for integrity checking. Pressure sensor 42, hydrocarbon sensor 50, and temperature sensor 44 provide additional means for release detection. A sensor station controller 38 with a temperature sensor inputs sensor values and transmits sensor and location data and status messages over the network power and data bus 11. The controller also communicates with a locally visible station status indication via a separate connection 86 on the sensor station.

The autonomous fluid spill containment device 10 is typically used as part of an autonomous sensor and reporting network that monitors pipeline spillage, as described above. The network interface is in communication with the device and is configured to transmit data from the device 10 to an analysis and response center.

Referring to FIG. 10, one or more sensor stations 30 communicate sensor data, location, status and other messages with a network monitor station 13 over a network power and data bus 11. Where the distances exceed data bus length capability, a sensor station configured as a repeater 31 performs a bridge between data busses 11, allowing a network bus length of up to approximately 10 miles.

Figure 11:
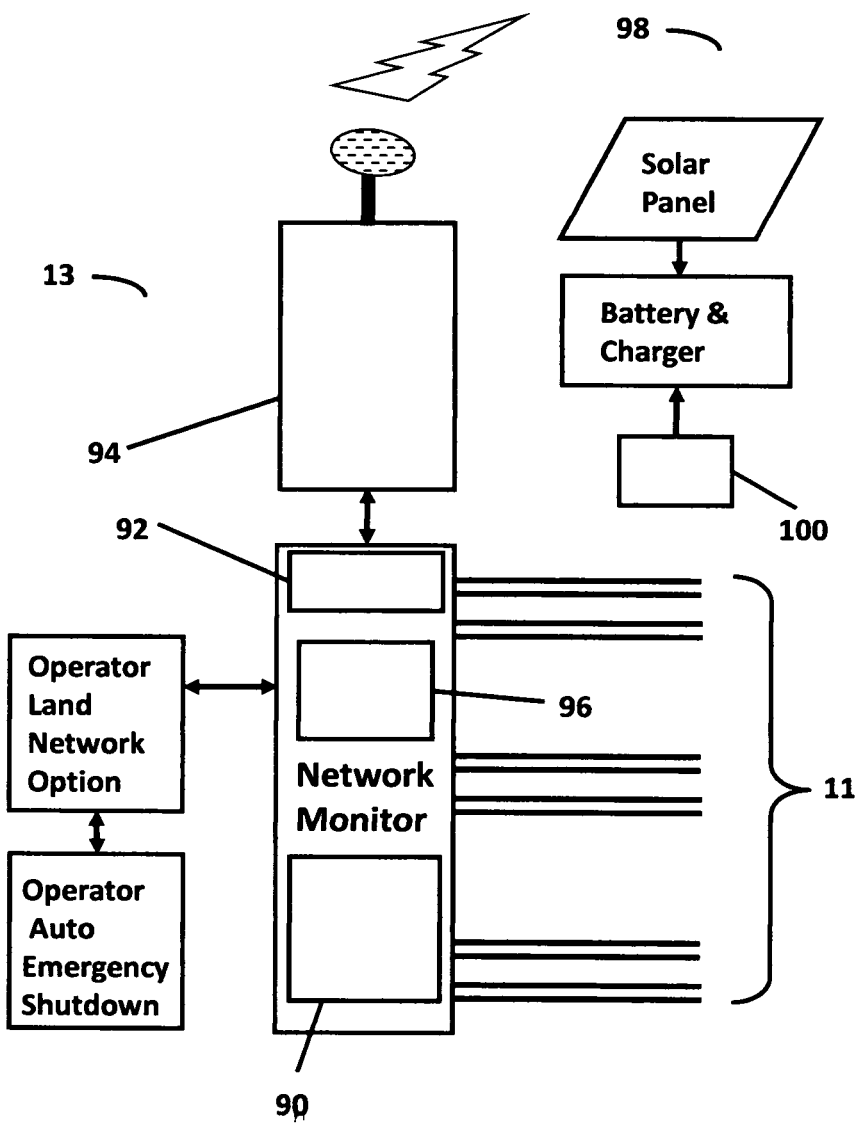
FIG. 11 is a diagrammatic representation of a network monitoring station.

Referring to FIG. 11, a network monitor station 13 forms the hub for the network power and data busses 11. Typically two data busses, one upstream and one downstream connect to one network monitor station 13. Additional connections allow one network monitor station 13 to connect to merging pipelines at or near the network monitor station location 13. The network monitor station 13 includes a display and control 90 for checkout and other servicing, and a modem 92 or other suitable means for communication with a remote satellite phone 94 and/or user wireless land network. A solar panel, battery and charger 98 provide autonomous remote location power. The user may elect to provide backup or alternate power 100 where available.

Still referring to FIG. 11, a network interface 96 option communicates with a user land network such as a SCADA (Supervisory Control And Data Acquisition) system or other system. In critical applications, the user may elect to use the network real time reporting capability to automatically shut down a pipeline segment until a release problem is resolved.

Figure 12:
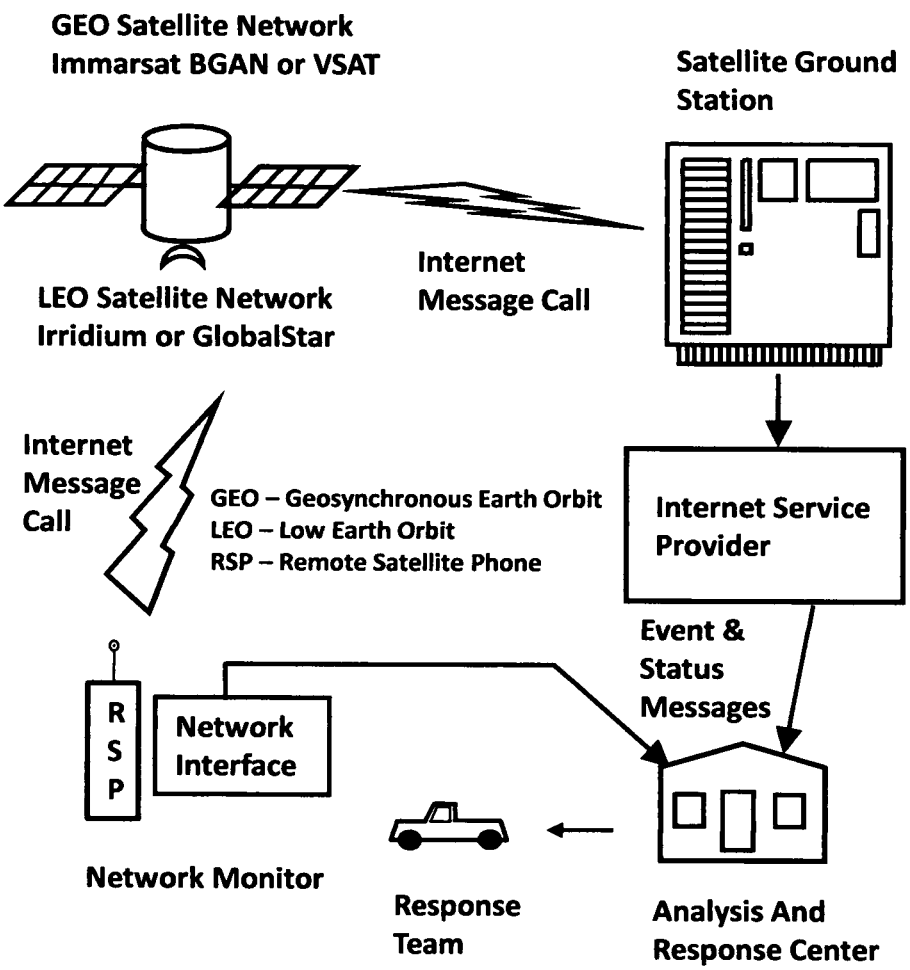
FIG. 12 is a diagrammatic representation of a sensor network reporting and response system Further details of the device and its advantages will be apparent from the detailed description included below.

Referring to FIG. 12, the sensor networks can use existing satellite and internet networks and user's land based networks to communicate sensor networks messages with the user's analysis and response center in real time. When a concern is identified in the analysis, the user response team is then dispatched to investigate and fix any problem.

Operation

The autonomous fluid spill containment device 10 is typically used as part of an autonomous sensor and reporting network that monitors pipeline spillage, as described above, and communicates with an analysis and response center as shown in FIG. 12. The center is located to receive data over a network from the device 10 such that real time data received at the center is indicative of a fluid spill which then triggers a response at the center. A satellite network may also be used to communicate with the device to relay data from the device to the center.

The network monitor station(s) provide the device 10 with centralized control and interfacing to external systems. The network monitor station sends messages to the sensor stations in turn, requesting sensor and location data, sensor health status and network status. The network monitor station assembles the response messages and analyzes the information, looking for critical fault indications, including non-reporting sensor stations. If any critical fault indications are found, a message is sent immediately to the pipeline operator's analysis and response center. Otherwise, the accumulated messages are sent to the analysis and response center on a schedule predetermined by the pipeline operator. The messages may be sent via satellite or via a land network as determined by the pipeline operator.

The sensor stations operate in a dual power mode to reduce power consumption, allowing adequate power to be delivered to longer sensor station networks. For the majority of the time, just the sensor station controller and network interface are powered and the sensor station controller listens for its messages. When a message tagged with the sensor station controller's identification is received, the controller switches sensor power on, collects sensor data, switches sensor power off, performs sensor data validity checks, and assembles and transmits the response message to the network monitor station.

Spill detection and containment is achieved using a dual coaxial pipe configuration in which an outer wall containment pipe surrounds a carrier pipe. Any fluid release is contained in the containment pipe. In the event there is a release from the carrier pipe, the transported material flows into the outer containment pipe. This flow of fluid into the containment pipe moves therealong until it reaches the end of the pipe component where it would reach the spill door which would facilitate transporting the material back into the carrier pipe. This brings the spill material in close proximity to the sensors, providing a quicker determination that a release is occurring. This shunting and redirecting of the material back into the carrier pipe at a further location down the line also promotes the safe and continued transport of the material until the crew can effect the necessary repairs. The pipeline system has at the location of each flow redirection spill door, a sensor station that in conjunction with temperature, pressure and liquid sensors, has the unique ability to autonomously sense and notify the owner/operator in real time as to the nature and location of any small or large concern. A visible station status indicator (e.g., a LED) located on or above the sensor station will serve to further assist the repair crew in locating the concern. In the event the spill door option is not implemented, or in the remote chance the spill door malfunctions, the system will continue to use the remaining sensors to detect and report the malfunction and presence of material in the containment pipe in real time.

The device 10 implements the use of a sensor station network system to autonomously report its findings and engage the response. This system is powered by solar energy and in conjunction with a battery and charger can be augmented with external power resources if available. The system can report via satellite link, allowing real time coverage in remote areas, and can connect directly to a user's monitoring and response system, to include automated shutdown of the affected pipeline to mitigate potential damage. This self monitoring, containment, and notification system is completely autonomous, easily repaired, and provides the owner/operator with a safe method to transport hazardous energy materials.

Release Reporting and Locating:

To achieve these results, the system implements a sensor network that uses three types of messages to achieve functionality. Additional message types may also be used for network administration, but are typical practice and will not be described here.
1. Sensor Health Status. Sensor outputs are checked for shorted or broken connections and internal sensor electronics failures. Sensor interface electronics performs internal and bus message checks. Sensor health status report messages including sensor station location are sent to the operator station.
2. Sensor Data. Sensor outputs are sampled periodically. Sensor data messages including sensor station and release detections location are sent to the operator station.
3. Network Status. Sensor stations and network monitors report any failure to communicate with a downlink station to the operator station. Each station has a unique identifier and known location.

The operator station processes the incoming messages by examining for release indications and by applying, e.g., trend and variance algorithms to the sensor data appropriate to the material being transported. Results are archived for future reference. The station displays results to the operator and triggers visual and aural alarms and related location for detected release events.

Transported Fluid Release Characteristics

To effectively detect transported material releases, the system is designed to monitor for the characteristics of the three types of releases—rupture, leak and seepage. Note that for a single wall pipe, release is an unintended loss of transported material to the pipeline surroundings. For a dual wall system, release includes loss from the inner carrier pipe to the outer containment pipe and ingestion from the surroundings into the containment pipe. Distinguishing characteristics of the three types of releases are:

Rupture—A high mass-rate release or ingestion caused by catastrophic pipeline failure. Typically occurs suddenly, and may be caused by external forces such as bulldozer, earth movement, sabotage, or other similar events, or the rapid progression of a pipeline structural failure.

Leak—A lower rate (but can still be substantial) release through a hole in the pipe smaller than the pipe diameter and does not progress significantly in size over a short time. A leak may occur suddenly from backhoe puncture, pilferage or other similar events or progress slowly from usage and environmental events such as corrosion, thermal stresses, or transported material abrasion.

Seepage—A very low rate release through a small hole or crack, typically caused by events such as corrosion, weld defects, or seal failure. The seepage may be intermittent, for example if a higher viscosity material plugs the opening after a previous lower viscosity material release, or an earth shift or ambient temperature change closes a crack.

Device Release Detection:

Release detection is based on the use of sensors at intervals in the container pipe monitoring characteristics such as pressure, temperature, spill door position, hydrocarbon vapors and liquid level. Sensor readings are transmitted in real time to a user's reporting station for analysis and action.

Rupture Detection:

A rupture causing a release from the carrier pipe is detected by a sudden change in temperature and/or pressure and/or door position and/or possibly liquid level or hydrocarbon level, depending on the transported material. Depending on the nature of the rupture, the sensor network may be damaged (albeit in rare circumstances) and stop reporting from that location, which in itself shall serve as a locator for the rupture.

Detecting a rupture causing ingestion is dependent on the extent of the failure. For ingestion in an unpressurized containment pipe, the likely detection will be a rise in liquid level from water ingestion, but this may take some time, or may not occur at all. If there is water ingestion, repair is required to avoid carrier pipe corrosion. If not, the repair is not time critical. In a pressurized containment pipe, there may be a slow pressure change if the pipe is buried, a fast change if not. If the cause is accidental human induced trauma such as excavation machinery, the operator may detect and report the event. If not, such as an act of terrorism or sabotage, the ingestion caused by this form of trauma will be detected by the sensors and reported.

Leak Detection:

Leak detection for both release and ingestion is the same as rupture detection, except that sensor readings will change more slowly, and the sensor network is unlikely to be damaged. Pilferage may or may not be detected, depending on the pilferer's ability to penetrate the double walls without causing a detectable change in sensor readings.

Seepage Detection:

Seepage is inherently difficult to detect because sensor readings may be masked by signal noise, and by normal changes in transported material and pipeline environment. In the device 10, seepage is detected by the liquid sensor and by the hydrocarbon sensor. For the critical case of transported material release, it is unlikely that there will be a concurrent seepage through the containment pipe to the environment. Ingestion is less critical, since the only significant effect is to accelerate corrosion of the carrier pipe. In both release and ingestion, detection allows adequate time for repair.

Although the above description relates to a specific embodiment as presently contemplated by the inventor, it will be understood that the device in its broad aspect includes mechanical and functional equivalents of the elements described herein.

We claim:

1. An autonomous fluid spill containment device for a pipeline having a carrier conduit for transporting a fluid and a containment conduit located around the carrier conduit to define an interstitial space for receiving fluid spilled from the carrier conduit, the device comprising:
   a spilled fluid barrier for stopping spilled fluid flow, the fluid barrier being located in the interstitial space and extending between the carrier conduit and the containment conduit;
   a spilled fluid sensor located in the interstitial space to detect spilled fluid flowing in the containment conduit;
   a network monitor that interfaces for communicating with an operator's data collection, analysis and reporting systems; and
   a sensor network connected to the fluid sensor for communicating spilled fluid sensor and location data from the sensor to the network monitor so as to alert the operator to the location of the spilled fluid in real time.

2. The device, according to claim 1, in which the spilled fluid sensor is located at a lower portion of the containment conduit.

3. The device, according to claim 2, in which the spilled fluid sensor is mounted on the spilled fluid barrier.

4. The device, according to claim 1, in which a sensor station is mounted exterior of the containment conduit, the sensor station being in communication with the spilled fluid sensor.

5. The device, according to claim 4, in which the sensor station includes:
   a) a housing;

b) a purge member located in the housing and in fluid communication with the interstitial space and a spilled fluid sensor; and
c) a sensor station network including a controller located in the housing, the controller being in communication with a purge member pressure sensor, a local status indicator for further facilitating accurate location of a spill/seepage, and the spilled fluid sensor.

6. The device, according to claim 5, in which the sensor station further includes a plurality of sensors interconnecting the controller and the sensor network.

7. The device, according to claim 6, in which the sensors include a pressure sensor, a temperature sensor, a fluid sensor, a position sensor, and a hydrocarbon sensor, one or more of the sensors may be implemented and activatable.

8. The device, according to claim 5, in which the sensor station further includes a network power and data bus in communication with the sensors.

9. The device, according to claim 5, in which the sensor station further includes a repeater.

10. The device, according to claim 5, in which the network monitor is interconnected with the sensor station network and includes a network modem, a network interface and a display/control.

11. The device, according to claim 5, in which the network is autonomously operable using solar power, battery and charger or alternate power.

12. The device, according to claim 10, in which the network monitor is in communication with an operator land and wireless networks.

13. The device, according to claim 12, in which the operator land and wireless networks are capable of communicating with an auto emergency shutdown.

14. The device, according to claim 4, includes a spill return door assembly located upstream from the spilled fluid barrier.

15. The device, according to claim 14, in which the spill return door assembly, when implemented, includes a spill return door resiliently connected to the carrier conduit and is urged against an interior portion of the carrier conduit adjacent a spill opening.

16. The device, according to claim 15, in which the spill door assembly includes a mounting column and a door spring connected to the spill return door.

17. The device, according to claim 16, in which the door spring is located in the housing exterior of the containment conduit.

18. The device, according to claim 16, in which the door spring is located in the containment conduit.

19. The device, according to claim 15, in which the spill door assembly includes a spill door position sensor.

20. The device, according to claim 1, in which a sensor station is mounted interior of the containment conduit, the sensor station being in communication with the spilled fluid sensor.

21. The device, according to claim 20, in which the sensor station includes a sensor station network having a plurality of sensors interconnecting the controller to the sensor network.

22. The device, according to claim 21, in which the sensors include a pressure sensor, a temperature sensor, a fluid sensor, a position sensor, and a hydrocarbon sensor, wherein one or more of the sensors may be implemented and activatable.

23. The device, according to claim 20, in which the sensor station further includes a network power and data bus interconnected to the sensors and in communication with an external sensor station providing autonomous or alternate power.

24. The device, according to claim 20, in which the sensor station further includes a repeater.

25. The device, according to claim 20, in which the network monitor is interconnected with the sensor station network and includes a network modem, a network interface and a display/control.

26. The device, according to claim 25, in which the network monitor is in communication with operator land and wireless networks.

27. The device, according to claim 26, in which the operator land and wireless networks are capable of communicating with an auto emergency shutdown.

28. The device, according to claim 20, includes a spill return door assembly located upstream from the spilled fluid barrier.

29. The device, according to claim 28, in which the spill return door assembly, when implemented, includes a spill return door resiliently connected to the carrier conduit and is urged against an interior portion of the carrier conduit adjacent a spill opening.

30. The device, according to claim 28, in which the spill door assembly includes a mounting column and a door spring connected to the spill return door.

31. The device, according to claim 28, in which the spill door assembly includes a spill door position sensor.

32. The device, according to claim 4, is for a pipeline that is located above ground, ice or water.

33. The device, according to claim 4, is for a pipeline that is located underground or in ice.

34. The device, according to claim 20, is for a pipeline that is located underwater.

35. The device, according to claim 20, is for a pipeline that is located above ground, ice or water.

36. The device, according to claim 20, is for a pipeline that is located underground or in ice.

37. The device, according to claim 1, in which the fluid includes gas, synthetic chemicals, organic chemicals, inorganic chemicals; and natural fluids including food liquids; liquefied natural gas, liquefied gas including propane and butane; crude oil, water, petroleum, light oil, or tar sands oil.

38. The device, according to claim 5, in which the local status indicator is an Light Emitting Diode (LED).

39. An autonomous sensor and reporting network for monitoring pipeline spillage, the network comprising:
a) an autonomous fluid spill containment device having a carrier conduit for transporting a fluid and a containment conduit located around the carrier conduit to define an interstitial space for receiving fluid spilled from the carrier conduit, the device having a spilled fluid barrier for stopping spilled fluid flow, the fluid barrier being located in the interstitial space and extending between the carrier conduit and the containment conduit; a spilled fluid sensor located in the interstitial space to detect spilled fluid flowing in the containment conduit; a network monitor that interfaces for communicating with an operator's data collection, analysis and reporting systems; and a sensor network connected to the fluid sensor for communicating spilled fluid sensor and location data from the sensor to the network monitor so as to alert the operator to the location of the spilled fluid in real time; and
b) a network interface in communication with the device, the network interface being configured to transmit sensor and location data from the device to an analysis and response center, the center being located to receive data over the operator's selection of wired and wireless networks from the device such that real time data received at the center indicative of a fluid spill triggers a response at the center.

40. The network, according to claim 39, in which the wireless network is a satellite network in communication with the device to relay data from the device to the center.

41. The network, according to claim 39, in which a wireless land network is in communication with the device to relay data from the device to the center.

42. The network, according to claim 39, in which a wired land network is in communication with the device to relay data from the device to the center.

43. An autonomous sensor and reporting system for monitoring pipeline spillage, the system comprising:
  a) an autonomous fluid spill containment device having a carrier conduit for transporting a fluid and a containment conduit located around the carrier conduit to define an interstitial space for receiving fluid spilled from the carrier conduit, the device having a spilled fluid barrier for stopping spilled fluid flow, the fluid barrier being located in the interstitial space and extending between the carrier conduit and the containment conduit; a spilled fluid sensor located in the interstitial space to detect spilled fluid flowing in the containment conduit; a network monitor that interfaces for communicating with an operator's data collection, analysis and reporting systems; and a sensor network connected to the fluid sensor for communicating spilled fluid sensor and location data from the sensor to the network monitor so as to alert the operator to the location of the spilled fluid in real time;
  b) an active network interface in communication with the device, the network interface being configured to transmit sensor and location data from the device to an analysis and response center, the center being located to receive data over the operator's selection of wired and wireless networks from the device such that real time data received at the center indicative of a fluid spill triggers a response at the center; and
  c) a real time self-monitoring and reporting system that determines sensor station health status, sensor data and network status in real time.

44. The system, according to claim 43, in which the wireless network is a satellite network in communication with the device to relay data from the device to the center.

45. The system, according to claim 43, in which a wireless land network is in communication with the device to relay data from the device to the center.

46. The system, according to claim 43, in which a wired land network is in communication with the device to relay data from the device to the center.

47. The system, according to claim 43, in which a dual wall pipe with an outer casement spilled fluid bather is utilized.

48. The system, according to claim 43, in which the sensor stations include a plurality of sensors whereby one or more are implemented and activatable including: pressure, temperature, fluid, position, and hydrocarbon.

49. The system, according to claim 43, in which the system implements a power supply that is a conventional energy supply or a solar panel, battery and charger.

50. The system, according to claim 43, which includes a spill door to facilitate transporting material from the outer containment conduit into the carrier conduit.

* * * * *